United States Patent [19]

Harandi et al.

[11] Patent Number: 4,992,607
[45] Date of Patent: Feb. 12, 1991

[54] PETROLEUM REFINERY PROCESS AND APPARATUS FOR THE PRODUCTION OF ALKYL AROMATIC HYDROCARBONS FROM FUEL GAS AND CATALYTIC REFORMATE

[75] Inventors: Mohsen N. Harandi, Lawrenceville, N.J.; John D. Kushnerick, Boothwyn, Pa.; Hartley Owen, Belle Mead, N.J.

[73] Assignee: Mobil Oil Corporation, New York, N.Y.

[21] Appl. No.: 325,736

[22] Filed: Mar. 20, 1989

[51] Int. Cl.⁵ .............................................. C07C 2/66
[52] U.S. Cl. ................................... 585/467; 585/322; 585/323
[58] Field of Search ................ 585/467, 323, 322

[56] References Cited

U.S. PATENT DOCUMENTS

| | | |
|---|---|---|
| 3,729,409 | 12/1970 | Nai Yuen Chen . |
| 3,751,506 | 8/1973 | Burress ................... 585/467 |
| 3,755,483 | 8/1973 | Burress . |
| 3,827,968 | 1/1973 | Givens et al. . |
| 3,907,663 | 9/1975 | Owen ..................... 585/467 |
| 4,016,218 | 4/1977 | Haag et al. . |
| 4,140,622 | 2/1979 | Herout et al. ............. 585/467 |
| 4,150,062 | 4/1979 | Garwood et al. . |
| 4,209,383 | 6/1980 | Herout et al. ............. 585/467 |
| 4,393,262 | 7/1983 | Kaeding . |
| 4,497,968 | 2/1985 | Wright et al. . |
| 4,542,251 | 9/1985 | Miller . |
| 4,827,069 | 5/1989 | Kushnerick et al. ............... 585/467 |

Primary Examiner—Asok Pal
Attorney, Agent, or Firm—Alexander J. McKillop; Charles J. Speciale; L. G. Wise

[57] ABSTRACT

A petroleum refinery process for the production of alkyl aromatic hydrocarbons from a $C_4{}^-$ fuel gas containing light olefins including ethene and propene and catalytic reformate containing $C_6$ to $C_8$ aromatics. The $C_4{}^-$ fuel gas is contacted with the catalytic reformate at a weight ratio of aromatics to olefins of 10:1 to 15:1 over a zeolite catalyst under process conditions to alkylate the $C_6$ to $C_8$ aromatics, particularly benzene, in the reformate with ethene and propene in the $C_4{}^-$ fuel gas to form alkyl aromatic hydrocarbons. The reaction is carried out in a riser reactor having multiple olefin feed injection points in the riser section of the reactor.
The catalytic reaction also causes the conversion of a small amount of light olefins in the fuel gas to coke by-product and the deposition of coke on the catalyst. The deposited coke causes the partial deactivation of the catalyst. A portion of the partially deactivated catalyst is continuously or intermittently withdrawn from the riser reactor and regenerated in a catalyst regenerator by contacting the catalyst with hydrogen containing regeneration gas or by contacting the catalyst with an oxygen containing regeneration gas to remove substantially all of the coke from the catalyst. The regenerated catalyst is introduced in the riser reactor and contacted with fresh feed.

28 Claims, 3 Drawing Sheets

PETROLEUM REFINERY PROCESS AND APPARATUS FOR THE PRODUCTION OF ALKYL AROMATIC HYDROCARBONS FROM FUEL GAS AND CATALYTIC REFORMATE

CROSS-REFERENCE TO RELATED APPLICATIONS

This application is related to Kushnerick et al U.S. Ser. No. 157,831 filed Feb. 19, 1988, which is assigned to applicant's assignee and which is incorporated herein by reference thereto.

FIELD OF THE INVENTION

The present invention relates to a petroleum refining process for the production of alkyl aromatic hydrocarbons suitable as gasoline blending stock. The present invention more specifically relates to the production of alkyl aromatic hydrocarbons by contacting a $C_4^-$ fuel gas containing light olefins including ethene and propene with a catalytic reformate containing $C_6$ to $C_8$ aromatics, particularly benzene, over a zeolite catalyst to form alkyl aromatic hydrocarbon gasoline. The process includes the catalytic reforming of naphtha to obtain the catalytic reformate feed and the fluid catalytic cracking of hydrocarbons to obtain the $C_4^-$ fuel gas feed to the zeolite catalyst conversion zone.

The process further includes regeneration of catalyst having coke deposited thereon by contacting the catalyst in a catalyst regenerator with a hydrogen containing regeneration gas or by contacting the catalyst with an oxygen containing regeneration gas to remove substantially all of the coke deposits from the catalyst.

BACKGROUND OF THE INVENTION

The fluid catalytic cracking of hydrocarbons in modern refinery operations produces large amounts of $C_4^-$ fuel gas containing light olefins of essentially no gasoline product value and the catalytic reforming of hydrocarbons produces large amounts of $C_6$ to $C_8$ aromatic hydrocarbons which though having value as gasoline blending stock are produced in excessive amounts. The petroleum refinery typically produces aromatics and light olefins on a mole ratio basis of aromatics to olefins of about 2:1 which is not suitable for directly carrying out a process for the alkylation of all of the aromatics that are produced.

The present invention particularly relates to a catalytic technique for alkylating $C_6$ to $C_8$ aromatics with light olefins to form heavier alkyl aromatic hydrocarbons. In particular, it provides a continuous process for alkylating $C_6$ $C_8$ aromatics, particularly benzene, contained in a catalytic reformate with ethene and propene contained in $C_4^-$ fuel gas to form $C_1$ to $C_4$ alkyl substituted aromatic hydrocarbons for use as gasoline blending stock. Ethene containing gases, such as petroleum cracking offgas, and catalytic reformate containing, for example, benzene, toluene, xylene and ethyl benzene are useful feedstocks for the process.

Developments in zeolite catalysis and hydrocarbon conversion processes have created interest in utilizing olefinic feedstocks for producing $C_5^+$ gasoline, diesel fuel, etc. In addition to basic chemical reactions promoted by ZSM-5 type zeolite catalysts, a number of discoveries have contibuted to the development of new industrial processes. These are safe, environmentally acceptable processes for utilizing feedstocks that contain lower olefins, especially $C_2$–$C_4$ alkenes and feedstocks containing aromatic compounds, especially $C_6$ to $C_8$ aromatics.

Chen U.S. Pat. No. 3,729,409 discloses improving the yield-octane number of a reformate by contacting the reformate in the presence of hydrogen over a zeolite catalyst. Garwood et al U.S. Pat. No. 4,150,062 discloses a process for the conversion of $C_2$ to $C_4$ olefins to produce gasoline which comprises contacting the olefins with water over a zeolite catalyst. The Haag et al U.S. Pat. No. 4,016,218 and Burress U.S. Pat. No. 3,751,506 disclose processes for the alkylation of benzene with olefins over a ZSM-5 type catalyst. The Heroute et al U.S. Pat. No. 4,209,383 discloses the catalytic alkylation of benzene in reformate with $C_3$–$C_4$ olefins to produce gasoline.

It has now been found that contacting a catalytic reformate feed comprising $C_6$ to $C_8$ aromatic hydrocarbons with a light olefin gas feed, comprising ethene, propene and/or butene at a weight ratio of aromatics to olefin of 10:1 to 15:1, over a zeolite catalyst that the $C_6$ to $C_8$ aromatics in the catalytic reformate can efficiently be converted to alkyl aromatic hydrocarbons which are suitable for use as gasoline blending stocks.

In accordance with the present invention refinery olefins and light aromatic hydrocarbons are upgraded to products of higher value in a practically most efficient manner.

SUMMARY OF THE INVENTION

The present invention is directed to a process for the production of gasoline which comprises the steps of fractionating a crude oil feed stream into a light distillate naphtha stream and a vacuum gas oil stream; passing the light distillate naphtha stream through a catalytic hydrotreating zone and then through a catalytic reforming zone to obtain a catalytic reformate stream containing $C_6$ to $C_8$ aromatic hydrocarbons; passing the vacuum gas oil stream into a fluidized catalytic cracking zone which includes a fractionating column and producing an overhead $C_4^-$ olefinic hydrocarbon fuel gas vapor stream; and contacting the catalytic reformate stream and the $C_4^-$ fuel gas stream in a zeolite catalyst riser reactor reaction zone under process conditions to form alkyl aromatic hydrocarbons. The alkyl aromatic hydrocarbons are suitable gasoline blending stock.

The present invention is more specifically directed to an improved process for the alkylation of $C_6$ to $C_8$ aromatics contained in a catalytic reformate with ethene-containing feedstocks to form lower alkyl aromatic hydrocarbon products of higher octane value wherein the feedstocks are contacted at elevated temperature and pressure with a fluidized zeolite aromatic hydrocarbons are contacted with the olefinic hydrocarbons over the zeolite catalyst at an aromatic to olefin weight ratio of 7:1 to 20:1.

The high weight ratio of aromatic hydrocarbons to olefin hydrocarbons in the riser reactor is achieved by utilizing a riser reactor design which employs multiple olefin feed injection points in the riser section of the reactor.

In accordance with the present invention a catalytic reformate rich in $C_6$ to $C_8$ aromatics can be efficiently alkylated with an ethene rich olefinic light gas feed to form alkyl aromatic hydrocarbons of higher octane value by catalytic conversion in a riser reactor utilizing fluidized solid solid acid zeolite catalyst.

The present invention also includes the regeneration of the catalyst in a catalyst regeneration zone.

The catalytic alkylation of aromatics with light olefins to form alkyl aromatic hydrocarbons by contact with a medium pore molecular sieve zeolite catalyst causes the deposition of coke by-product on the catalyst and the absorption of hydrocarbon product by catalyst. The coke deposition causes the partial deactivation of the catalyst. In order to overcome the catalyst deactivation it is necessary to remove partially deactivated catalyst from the reactor and to remove the coke deposits from the catalyst. The coke deposits are removed in a regeneration zone by contacting the catalyst with a hydrogen containing regeneration gas or by contacting the catalyst with an oxygen containing gas to effect combustion of the coke of the coke.

The present invention is particularly useful for upgrading FCC light gas, which usually contains significant amounts of ethene, propene and/or butene and for upgrading catalytic reformate which usually contains significant amounts of benzene, toluene, xylene and ethyl benzene.

ADVANTAGES

The process of the present invention because of the use of multiple olefin feed injection points in the riser reactor maintains a high weight ratio of aromatics to olefins during the reaction and obtains a maximum conversion of light olefins and aromatics to alkyl aromatics. The high weight ratio of aromatics to light olefins in the riser reactor also minimizes olefin oligomerization reactions and minimizes coke formation and coke deposition on the catalyst.

The regeneration of coked catalyst by contacting the catalyst in a regeneration zone with a hydrogen containing regeneration catalyst converts the coke deposits to hydrocarbons and increases overall hydrocarbon yield of the process.

OBJECTS OF THE INVENTION

It is an object of the present invention to provide a novel integrated refinery process for increasing the overall production of gasoline products.

It is another object of the present invention to reduce the overall fuel gas production and $C_6$ to $C_8$ aromatics, particularly benzene, production of the refinery while at the same time increasing gasoline product production.

It is a further object of the present invention to provide a novel economical process for alkylating aromatic hydrocarbons, by contacting a hydrocarbon stream containing $C_6$ to $C_8$ aromatic hydrocarbons, particularly benzene, with a feed stream containing light olefins, including ethene, propene and/or butene with fluidized zeolite catalyst in a riser reactor to form alkyl aromatic hydrocarbon gasoline products.

It is a further object of the present invention to provide an efficient method of regenerating partially deactivated catalyst containing coke deposits by contacting the catalyst in a catalyst regeneration zone with a hydrogen containing regeneration gas.

It is a further object of the present invention to provide an efficient method of regeneration partially deactivated catalyst containing coke deposits by contacting the catalyst in a catalyst regeneration zone with an oxygen containing regeneration gas under conditions of combustion of the coke and removal of the coke from the catalyst.

DETAILED DESCRIPTION OF THE INVENTION

Figure 1:
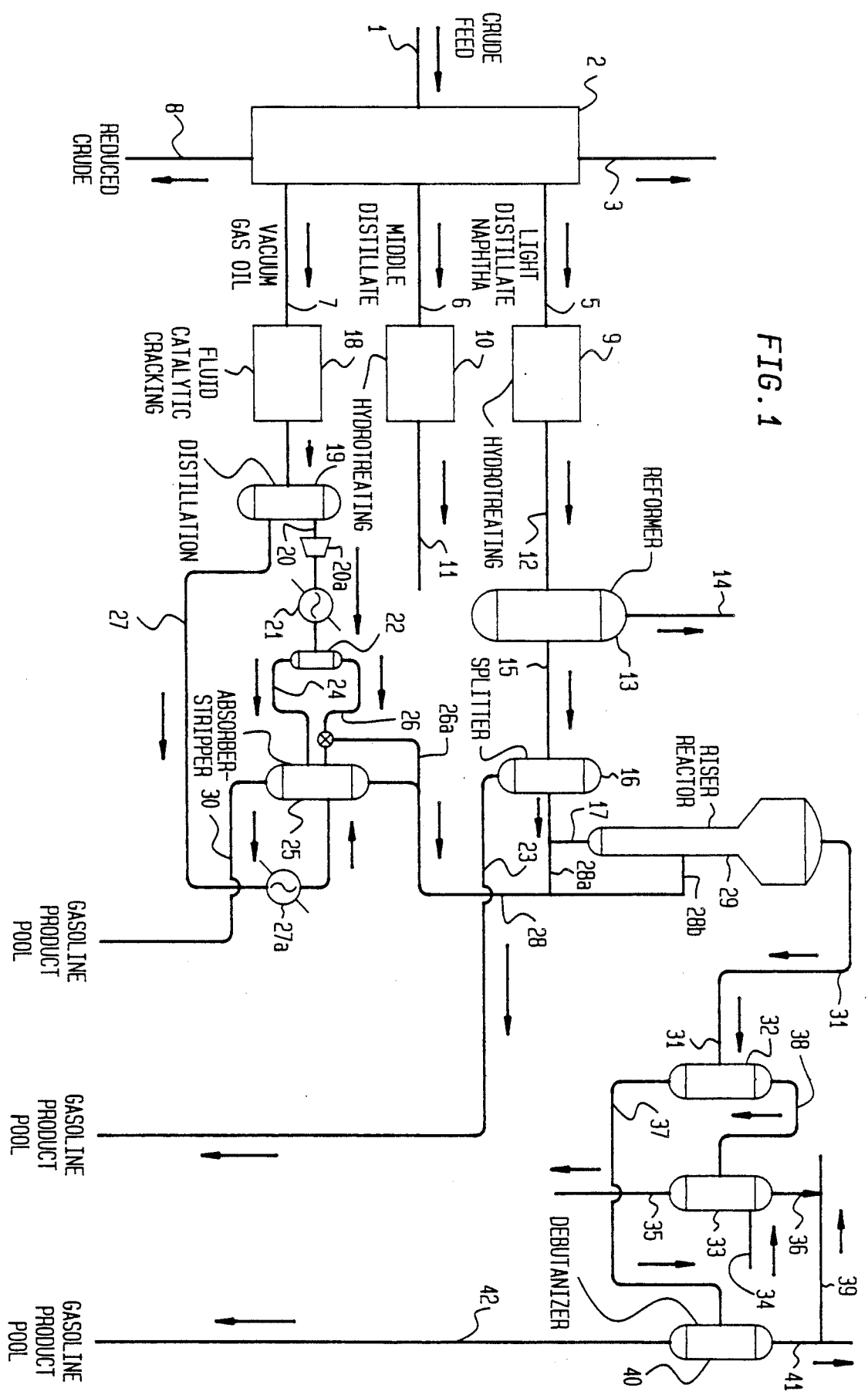
FIG. 1 of the drawings is a flow diagram of the petroleum refining process of the present invention for the production of gasoline.

The present invention utilizes conventional petroleum refining steps including fractionation, hydrotreating, catalytic, reforming and fluidized catalytic cracking and a novel zeolite catalyst process utilizing a riser reactor to upgrade the fuel gas and reformate process streams. A gasoline boiling range alkyl aromatic hydrocarbon product is produced from the fuel gas stream from the fluidized catalytic cracking process step and the reformate stream from the catalytic reforming step.

In accordance with the present invention crude oil feed is subjected to distillation to separate several hydrocarbon streams including a light gas, a gasoline boiling range light distillate naphtha, a middle distillate, a vacuum gas oil and a bottoms or reduced crude stream.

The naphtha stream is hydrotreated to remove sulfur and nitrogen compounds and then fed to a catalytic reforming zone wherein the octane value of this stream is increased, the concentration of aromatic hydrocarbons is increased and hydrogen is produced as a by-product.

The middle distillate stream is hydrotreated to produce products such as kerosene and jet fuel.

The vacuum gas oil is fed to a fluidized catalytic cracking (FCC) zone in which there is produced a light gasoline boiling range distillate, a fuel gas containing $C_1$ to $C_4$ olefins and paraffins and a heavy distillate. The FCC unit includes a fluidized bed molecular sieve catalytic cracker and a catalyst regenerator. The molecular sieve catalyst is continuously regenerated in the regenerator by oxidatively removing coke deposits from the catalyst by burning with air regeneration gas.

The reduced crude may be fed into a subatmospheric pressure or vacuum fractionation column. The reduced crude may also be subjected to processing steps such as propane deasphalting, hydrocracking, etc.

The catalytic reformate containing $C_6$ to $C_8$ aromatic hydrocarbons and the fuel gas stream containing $C_1$ to $C_4$ olefins and paraffins are fed to a fluidized zeolite catalyst reaction zone in a riser reactor. The riser reactor containing the zeolite catalyst is operated under conditions such that the weight ratio of aromatics to olefins is about 10:1 to 15:1 and the $C_4^-$ olefins, e.g. ethene and propene in the fuel gas feed stream alkylate the $C_6$ to $C_8$ aromatic hydrocarbons, particularly benzene, in the reformate feed stream to form $C_7$ to $C_{11}$ alkyl aromatic hydrocarbons such as toluene, xylene, ethyl benzene, methyl ethyl benzene, diethyl benzene, propyl benzene and methyl propyl benzene.

The effluent hydrocarbon stream from the riser reactor is passed into a separator in which a light hydrocarbon overhead stream, e.g. $C_{4-}$ hydrocarbons, is withdrawn and fed to an absorber in which a major portion of the $C_3^+$ hydrocarbons are absorbed and removed. The remaining $C_3^-$ hydrocarbons are taken overhead and can be recycled to the zeolite catalyst reaction zone. The bottoms from the separator contain $C_5^+$ hydrocarbons including the $C_7$ to $C_{11}$ alkyl aromatic hydrocarbons and are fed to a debutanizer from which an overhead $C_4^-$ gas stream is removed. The debutanized gasoline product is removed as a bottoms product and is fed to the gasoline product pool.

The catalyst in the riser reactor is continuously or intermittently withdrawn and regenerated in a catalyst regeneration zone. The catalyst can be regenerated by contact with a hydrogen containing regeneration gas or with an oxygen containing regeneration gas. Prior to carrying out the regeneration step the catalyst can be contacted in a stripping zone with an inert stripping gas such as nitrogen or steam to remove hydrocarbons absorbed on the catalyst.

DESCRIPTION OF FIG. 1 OF THE DRAWINGS

A crude oil feed is fed through line 1 to a crude oil distillation unit 2 and is separated into fractions having different boiling point ranges. The $C_3$ to $C_4$ light hydrocarbons and any gases dissolved in the feed are removed overhead through line 3 and passed to a gas recovery zone. The light normally liquid hydrocarbons are removed as a light distillate naphtha stream through line 5, a middle distillate stream through line 6, and a vacuum gas oil stream through line 7. The remaining reduced crude is removed through line 8 for further processing.

The naphtha fraction and the middle distillate fraction are passed to hydrotreating zones 9 and 10, respectively. The middle distillate hydrotreated stream is removed in line 11 and is in the kerosene boiling range hydrocarbons. The hydrotreated naphtha stream is passed through line 12 to a reforming zone 13 wherein it is catalytically reformed to produce a reformate containing $C_6$ to $C_8$ aromatic hydrocarbons and $C_6^+$ paraffinic hydrocarbons and hydrogen. The hydrogen is removed, as a by-product, overhead in line 14. The catalytic reformate is fed through line 15 to a fractionating column or splitter 16 in which a portion of the $C_6^+$ paraffinic hydrocarbons can be removed through line 23 and fed to the gasoline product pool. The hydrocarbons in line 17 are fed to riser reactor 29 and contain $C_6$ to $C_8$ aromatic hydrocarbons, particularly benzene, any remaining unseparated $C_6^+$ paraffinic hydrocarbons and may include $C_6^-$ paraffinic hydrocarbons of the catalytic reformate. Alternatively, particularly with light reformate streams, the fractionating step can be omitted and the entire reformate effluent stream can be fed directly to the riser reactor 29.

The vacuum gas oil removed through line 7 is fed to a fluidized bed catalytic cracking zone 18 which includes a fractionating column 19. The overhead vapor stream from the fractionating column 19 is removed in line 20, is compressed in compressor 20a and is cooled and condensed in condenser 21 and then fed to receiver 22. The condensate collected in receiver 22 is fed through line 24 to a primary absorber 25. The uncondensed gases in receiver 22 containing $C_4^-$ olefins are removed overhead through line 26 and fed to primary absorber 25. Alternatively, the uncondensed gases in receiver 22 containing the $C_4^-$ olefins can be fed via lines 26, 26a and 28 directly to the riser reactor 29. A liquid stream is removed from the fluid catalytic cracker fractionating column 19 through line 27, is cooled in heat exchanger 27a and is fed to the top of the primary absorber 25. An overhead gas stream including $C_4^-$ olefins is removed in line 28 and is fed through lines 28a and 28b to zeolite catalyst riser reactor 29 in which it is contacted with the catalytic reformate including $C_6$ to $C_8$ aromatics, particularly benzene, fed through the line 17.

The bottom line 30 from the primary absorber 25 containing $C_5^+$ gasoline product is debutanized and treated, by means not shown, and is fed to the gasoline product pool.

The ethene and propene in the $C_4^-$ feed in lines 28, 28a and 28b are contacted with the $C_6$ to $C_8$ aromatics, particularly benzene in the catalytic reformate that are fed to the riser reactor through line 17 and alkylate the aromatic hydrocarbons in riser reactor 29 to form alkyl aromatic hydrocarbon gasoline product. The riser reactor 29 product is removed from the reaction zone via line 31 and passed to separator 32. The overhead vapor products from separator 32 are fed via line 38 to absorber 33 and contacted with a suitable absorber oil fed through line 34 to remove $C_3^+$ hydrocarbons and absorber oil in line 35. The overhead line 36 from absorber 33 contains $C_3^-$ hydrocarbons. The absorber oil and $C_3^+$ hydrocarbons in line 35 are treated to separate the $C_3^+$ hydrocarbons and recycle the absorber oil. The bottoms from separator 32 is removed via line 37 and comprises the $C_5^+$ hydrocarbon and $C_7$ to $C_{11}$ alkyl aromatic hydrocarbon gasoline products and is fed to debutanizer 40 from which an overhead $C_4^-$ gas stream is removed via line 41.

The debutanized alkylated aromatic hydrocarbon gasoline product is removed via line 42 and is fed to the gasoline product pool.

The fractionation column or splitter 16 when used functions to control the amount and composition of the $C_6$–$C_8$ light aromatic hydrocarbon stream that is fed to reaction zone 29. The bottom line 23 from separator 16 contains $C_8^+$ gasoline product. The $C_6$–$C_8$ aromatic hydrocarbon stream contains primarily $C_6$–$C_8$ aromatic hydrocarbons and $C_5$ to $C_8$ paraffin hydrocarbons.

The zeolite catalyst riser reactor 29 is maintained at conditions of temperature and pressure such that the ethene and propene in the $C_4^-$ olefin stream alkylate the $C_6$ to $C_8$ aromatics in the catalytic reformate stream to form $C_7$ to $C_{11}$ aromatic hydrocarbons.

For purposes of clarity in the above description of the invention various subsystems and apparatus normally associated with the operation of the process have not been shown. The omitted items include pump, temperature, pressure and flow control systems, reactor and fractionator internals, crude column strippers, separators, reboilers, overhead condensing systems, etc. which may be of conventional design.

DESCRIPTION OF THE ZEOLITE CATALYST

Recent developments in zeolite technology have provided a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, B or Fe, within the zeolitic framework. These medium pore zeolites are favored for acid catalysis; however, the advantages of ZSM-5 structures may be utilized by employing highly siliceous material or crystalline metallosilicate having one or more tetrahedral species having varying degrees of acidity. ZSM-5 crystalline structure is readily recognized by its X-ray diffraction pattern, which is described in U.S. Pat. No. 3,702,866 (Argauer, et al.), incorporated by reference.

The zeolite catalysts preferred for use herein include the medium pore (i.e., about 5–7A) shape-selective crystalline aluminosilicate zeolites having a silica-to-alumina ratio of at least 12, a constraint index of about 1 to 12 and acid cracking activity of about 1–200. In an operating reactor the coked catalyst may have an apparent activity (alpha value) of about 1 to 80 under the process conditions to achieve the required degree of reaction severity. Representative of the ZSM-5 type zeolites are ZSM-5, ZSM-11, ZSM-12, ZSM-22, ZSM-23, ZSM-35 and ZSM-38. ZSM-5 is disclosed in U.S. Pat. No. 3,702,886 and U.S. Pat. Re. No. 29,948. The ZSM-5 and ZSM-12 catalyst are preferred. Other suitable zeolites are disclosed in U.S. Pat. Nos. 3,709,979; 3,832,449; 4,076,979; 4,076,842; 4,016,245 and 4,046,839; 4,414,423; 4,417,086; 4,517,396 and 4,542,251. The disclosures of these patents are incorporated herein by reference. While suitable zeolites having a coordinated metal oxide to silica molar ratio of 20:1 to 200:1 or higher may be used, it is advantageous to employ a standard ZSM-5 having a silica alumina molar ratio of about 25:1 to 70:1, suitably modified. A typical zeolite catalyst component having Bronsted acid sites may consist essentially of aluminosilicate ZSM-5 zeolite with 5 to 95 wt. % silica and/or alumina binder.

Certain of the ZSM-5 type medium pore shape selective catalysts are sometimes known as pentasils. In addition to the preferred aluminosilicates, the borosilicate, ferrosilicate and "silicalite" materials may be employed. It is advantageous to employ a standard ZSM-5 having a silica:alumina molar ratio of 25:1 to 70:1 with an apparent alpha value of 1–80 to convert 80 to 100 percent, preferably at least 90%, of the $C_2$–$C_3$ olefins in the feedstock and to convert 1 to 50% preferably at least 5% of the $C_6$–$C_8$ aromatics in the feedstock.

ZSM-5 type pentasil zeolites are particularly useful in the process because of their regenerability, long life and stability under the extreme conditions of operation. Usually the zeolite crystals have a crystal size from about 0.01 to over 2 microns or more, with 0.02–1 micron being preferred. The zeolite catalyst crystals are normally bound with a suitable inorganic oxide, such as silica, alumina, etc. to provide a zeolite concentration of about 5 to 95 wt. %. A preferred catalyst comprises 25% to 65% H-ZSM-5 catalyst contained within a silica-alumina matrix binder and having a fresh alpha value of less than 80.

When employing a ZSM-5 type zeolite catalyst in fine powder form such a catalyst should comprise the zeolite suitably bound or impregnated on a suitable support with a solid density (weight of a representative individual particle divided by its apparent "outside" volume) in the range form 0.6–2 g/cc, preferably 0.9–1.6 g/cc. The catalyst particles can be in a wide range of particle sizes up to about 250 microns, with an average particle size between 20 and 100 microns, preferably in the range of 10–150 microns and with the average particle size between 40 and 80 microns. When these solid particles are placed in a reactor bed where the superficial fluid velocity is 0.3–2 m/sec, fluidized bed operation is obtained. The velocity specified here is for an operation at a total reactor pressure of about 0 to 30 psig (100 to 300 kPa). Those skilled in the art will appreciate that at higher pressures, a lower gas velocity may be employed to ensure fluidized bed operation.

In the fluidized bed embodiment of the present invention it is advantageous to employ a particle size range consisting essentially of 1 to 150 microns. Average particle size is usually about 20 to 100 microns, preferably 40 to 80 microns. Particle distribution may be enhanced by having a mixture of larger and smaller particles within the operative range, and it is particularly desirable to have a significant amount of fines. Close control of distribution can be maintained to keep about 10 to 25 wt % of the total catalyst in the reaction zone in the size range less than 32 microns. This class of fluidizable particles is classified as Geldart Group A.

The light paraffin production and alkyl aromatic production is promoted by the zeolite catalysts having a high concentration of Bronsted acid reaction sites. Accordingly, an important criterion is selecting and maintaining the catalyst to provide either fresh catalyst having acid activity or by controlling catalyst deactivation and regeneration rates to provide an apparent average alpha value of about 1 to 50.

HYDROCARBON FEED STREAMS TO ZEOLITE CATALYST REACTION ZONE LIGHT OLEFIN GAS

The preferred light olefin gas feedstock contains $C_2$ to $C_4$ alkenes (mono-olefins), wherein the total $C_2$–$C_4$ alkenes are in the range of 10 to 40 wt %. Non-deleterious components, such as methane, $C_2$ to $C_4$ paraffins and inert gases, may be present. Some of the paraffins will be converted to $C_4+$ hydrocarbons depending on the reaction conditions and catalyst employed. A particularly useful feedstock is a light gas by-product of FCC gas oil cracking units containing typically 10–40 mol % $C_2$–$C_3$ olefins and 5–35 mol % $H_2$ with varying amounts of $C_1$ to $C_3$ paraffins and inert gas, such as $N_2$. The feedstock can contain primarily ethene, propene and/or butene.

The light olefin feed gas is described in more detail in the Table 1 below.

TABLE 1

| Weight % | Broad | Intermediate | Preferred |
|---|---|---|---|
| $H_2$ | 0 to 10 | 1 to 10 | 1 to 4 |
| Ethene | 1 to 99 | 8 to 50 | 8 to 35 |
| Propene | 0 to 99 | 3 to 50 | 3 to 40 |
| Ethene/Propene | 1 to 99 | 5 to 80 | 5 to 60 |

CATALYTIC REFORMATE

The catalytic reformate feedstock contains $C_6$ to $C_8$ aromatic hydrocarbons and $C_5$ to $C_8$ paraffinic hydrocarbons. The $C_6$ to $C_8$ aromatic hydrocarbons include benzene, toluene, xylene and ethyl benzene. The xylene and ethyl benzene are herein considered together as $C_8$ aromatic hydrocarbon. All or part of the $C_5$ to $C_6$ paraffinic hydrocarbons may be removed from the reformate stream prior to reacting the reformate with the light olefins. Though the catalytic reformate is a preferred feedstock, hydrocarbon process streams containing essentially the same hydrocarbon components can also be used.

The catalytic reformate feedstock is described in more detail below Table 2.

TABLE 2

|  | Broad | Intermediate | Preferred |
|---|---|---|---|
| Specific Gravity | 0.72 to 0.88 | 0.76 to 0.88 | 0.76 to 0.83 |
| Boiling Range, °F. | 60 to 400 | 80 to 400 | 120 to 320 |
| Weight % |  |  |  |
| Benzene | 1.0 to 99 | 2 to 60 | 10 to 40 |
| Toluene | 2.0 to 60 | 10 to 40 | 10 to 35 |
| $C_8$ Aromatic[1] | 0 to 60 | 0 to 50 | 0 to 8 |
| $C_6$-$C_8$ Aromatics | 5 to 100 | 10 to 95 | 35 to 75 |

[1] Xylene and ethyl benzene component.

HYDROCARBON PRODUCTS

The contacting of the light olefin gas feed with the catalytic reformate feed over the zeolite catalyst in accordance with the present invention produces the following products.

The ethene and propene components of the light olefin gas feed react with and alkylate the $C_6$ to $C_8$ aromatics in the catalytic reformate feed to produce primarily $C_7$ to $C_{11}$ alkyl aromatic hydrocarbons which may themselves rearrange and transalkylate over the zeolite catalyst.

The $C_7$ to $C_{11}$ alkyl aromatic hydrocarbon product obtained includes $C_1$ to $C_4$ lower alkyl substituted aromatic hydrocarbons such as methyl, ethyl, propyl and butyl benzene compounds. The $C_7$ to $C_{11}$ alkyl aromatic hydrocarbon product contains one or more of the foregoing lower alkyl substituents, providing however that the total number of carbon atoms in the substituents does not exceed 5. Typical $C_7$ to $C_{11}$ aromatic hydrocarbons, i.e. alkyl aromatic hydrocarbons, include toluene, ethyl benzene, xylene methyl ethyl benzene, propyl benzene, trimethyl benzene methyl propyl benzene, butyl benzene, tetra-methyl benzene, methyl butyl benzene and diethyl benzene.

The $C_7$-$C_{11}$ alkyl aromatic hydrocarbons have a higher octane value than the starting materials and enrich the overall octane quality of the gasoline blending stock.

The zeolite catalyst process conditions of temperature and pressure, and the weight ratio of aromatics to olefins of 10:1 to 15:1 are closely controlled to minimize and substantially eliminate olefin oligomerization reactions and are important features of the present invention.

Unreacted aromatic feed can be recycled to the riser reactor.

The ethene and propene in the light olefin feed are converted to alkyl aromatics in an amount of 80 to 100, preferably 90 to 100 and more preferably 95 to 100 wt. % of the olefin feed.

The $C_6$ to $C_8$ aromatics in the catalytic reformate feed, including benzene, toluene and $C_8$ aromatics, are converted to alkyl aromatics in an amount of 5 to 80 and preferably 20 to 50 wt. % of the feed.

The pores and the voids of the catalyst withdrawn from the riser reactor are filled with hydrocarbon product. The catalyst also contains deposited coke. The hydrocarbon product can be stripped from the catalyst by contacting the catalyst in a stripper vessel with an inert stripping gas prior to regenerating the catalyst. The catalytic coke remains on the catalyst and is removed during the catalyst regeneration step.

BY-PRODUCTS

An undesirable by-product of the catalytic reaction is the formation of a small amount of catalytic coke which deposits on the catalyst primarily as a result of olefin oligomerization reactions and which after a period of time builds up and partially deactivates the catalyst. The term coke as used herein is intended to mean nonvolatile carbonaceous material consisting primarily of highly condensed aromatic hydrocarbons.

RISER REACTOR

The process of the present invention is carried out in a riser reactor having multiple olefin feed injection points in the riser section of the reactor. The process utilizes a ZSM-5 type zeolite catalyst and the alkylation of the aromatic hydrocarbons by the light olefins is carried out primarily in the riser section of the reactor, though some conversion can take place in an upper fluidized bed section of the reactor.

The reaction temperature in the riser section of the reactor is 350° to 900° F. (177° to 482° C.), preferably 500° to 800° F. (260° to 427° C.) and more preferably 600° to 750° F. (315° to 399° C.). The reaction pressure in the riser section of the reactor is 20 to 650 psig (240 to 4580 kPa), preferably 120 to 420 psig (930 to 3000 kPa) and more preferably 150 to 250 psig (1140 to 1830 kPa).

The weight ratio of catalyst to reformate feed can be 0.5:1 to 50:1, preferably 1:1 to 10:1 and more preferably 3:1 to 7:1. The weight ratio of aromatic hydrocarbon to olefin hydrocarbon throughout the reaction is higher than 5:1, e.g. 7:1 to 20:1, preferably is 10:1 to 20:1 and more preferably 12:1 to 15:1.

The transfer gas velocity in the riser transfer regime section of the reactor 5 to 100 ft/sec (1.5 to 30 m/sec), preferably 5 to 30 ft/sec (1.5 to 9.1 m/sec) and more preferably 10 to 20 ft/sec (3 to 6.1 m/sec).

The use of an upper fluidized bed is an alternative embodiment of the invention. The riser reactor can be used without an upper fluidized bed.

The fluidizing gas velocity in the upper fluid bed section of the reactor, when the upper fluidized bed is used, can be is 0.3 to 4 ft/sec (0.1 to 1.2 m/sec), preferably 1 to 3 ft/sec (0.3 to 0.9 m/sec) and more preferably 1 to 1.5 ft/sec (0.3 to 0.5 m/sec). The upper fluid bed section of the reactor is preferably operated as a turbulent regime fluidized bed.

The riser section of the reactor can be 10 to 100 ft (3 to 30 m), typically 20 to 60 ft (6 to 18 m) in height. The diameter of the riser section can be 0.1 to 1 ft (0.03 to 0.3 m), typically 0.1 to 0.5 ft (0.03 to 0.15 m).

There can be 2 to 8, e.g. 2 to 6, typically 2 to 4 olefin feed injection points along the height of the riser reactor. This number of feed injection points includes the feed injection point at the bottom of the riser reactor. The multiple feed injection points are spaced 5 to 25 feet, typically 5 to 15 feet apart, along the height of the reactor, preferably along the height of the riser section, with the first one in the bottom of the reactor.

An olefin feed injection point can, however, be provided in the upper fluidized catalyst bed section of the reactor, and would be included in the above numbered olefin feed injection points. The multiple olefin feed injection maintains the desired high aromatic to olefin ratios in the reaction zone during the reaction.

The olefin feed can be substantially uniformly distributed through the multiple feed points so as to maintain in the riser reactor a weight ratio of aromatics to olefins in the riser section of the reactor and/or in the upper fluidized catalyst bed section of 7:1 to 20:1, preferably 10:1 to 15:1.

The fluidized bed section of the riser reactor, when used, can be 5 to 30 ft (1.5 to 9.1 m), typically 5 to 20 ft in height. The fluidized bed diameter can be 1 to 30 ft (0.3 to 9.1 m), typically 2 to 6 ft (0.6 to 1.8 m).

Catalyst particles are disengaged from the hydrocarbon gas product in a top dilute phase of the reaction zone in one or more internal gas solid separation cyclones or in an external sintered metal filter. All or at least a portion of the separated catalyst is returned to the riser reactor.

The alkyl aromatic hydrocarbon product gas is removed from the top of the reactor at a temperature of 400° to 800° F. (204° to 427° C.), preferably 600° to 750° F. (315° to 399° C.) and more preferably 650° to 750° F. (315° 399° C.) and more preferably 650° to 750° F. (343° to 399° C.) and taken for further processing.

The alkylation reaction converts a small portion of the light olefin feed to undesirable coke by-product primarily due to olefin oligomerization reactions which coke deposits on the catalyst and as the coke builds up partially deactivates the catalyst.

The riser reactor process conditions are controlled to maximize yield of alkyl aromatic hydrocarbons and to minimize coke by-product production. The alkylation reaction is promoted by the zeolite catalyst having a high concentration of Bronstead acid action cites. Accordingly, an important criteria is selecting and maintaining catalyst inventory to provide either fresh catalyst having acid activity or by controlling catalyst deactivation and regeneration rates to provide an apparent alpha value of 1–80.

The uniform contact of reformate and olefin and catalyst obtained in the riser section and in the upper fluidized bed section of the riser reactor, when used, provides close control of contact time between vapor and liquid and solid phases. The hydrocarbon feed and catalyst contact time in the riser section of the reactor is typically about 1 to 20 seconds and preferably 3 to 10 seconds.

An important feature of the present invention is that in the riser section of the reactor back mixing of the catalyst and aromatic and olefin feed is maintained at a minimum in order to maintain the desired high weight ratio of aromatic to olefin substantially throughout the reaction zone during the reaction which maximizes the yield of alkyl aromatic hydrocarbons.

The principle reactants in the process are the ethene and propene and/or butene constituents of the light olefin feed gas and the $C_6$ to $C_8$ aromatic constituent, particularly benzene, of the catalytic reformate and the weight ratio of aromatic to olefins are given in terms of these components.

Fine catalyst particles may be included in the reactor, especially due to attrition, and the fines may be entrained in the product gas stream. A typical riser reactor employs a temperature controlled catalyst zone with gas or liquid feed quench, whereby the reaction temperature can be controlled in the desired operating temperature range.

The reaction temperature may be in part controlled by exchanging hot reactor effluent with feedstock and/or recycle streams. Optional heat exchangers may recover heat from the effluent stream prior to fractionation. Part or all of the reaction heat can be removed from the reactor by using cold feed, whereby reactor temperature can be controlled by adjusting feed temperature.

CATALYST REGENERATION

The partially deactivated catalyst containing deposited coke and absorbed hydrocarbons can be regenerated by contacting the catalyst in a catalyst regeneration zone with a hydrogen containing gas or by contacting the catalyst with an oxygen containing gas.

HYDROGEN REGENERATION

In order to regenerate the catalyst and to recover the absorbed hydrocarbon product contained in the catalyst pores and voids, a portion of the partially deactivated catalyst containing the deposited coke and absorbed hydrocarbon product is continuously or intermittently withdrawn from the upper portion of the riser reactor or from the fluidized bed (when used) and transferred to a catalyst regeneration zone. About 40 to 800 %/hr, preferably 10 to 200 %/hr and more preferably 12 to 170 %/hr of the catalyst inventory in the riser reactor is withdrawn for regeneration.

The catalytic coke make is typically 0.005 to 1 wt. %, e.g. 0.005 to 0.3 wt. % and more typically 0.005 to 0.1 wt. % of the olefin feed. In accordance with an embodiment of the present invention the coke make is within the range of 0.001 to 0.025, for example 0.001 to 0.020 wt. % based on olefin feed.

The partially deactivated catalyst is contacted in the catalyst regenerator with hydrogen gas from the catalytic reformer. The hydrogen gas is fed into the bottom of the regenerator at a sufficient rate to maintain the catalyst as a fluidized bed.

The catalyst regeneration zone temperature is maintained at 450° to 1400° F. (232° to 760° C.), preferably 700° to 1200° F. (371° to 649° C.) and more preferably 700° to 1000° F. (371° to 538° C.). The catalyst regeneration zone pressure is generally maintained at about the same operating pressure as the riser reactor. The regenerator, however, can be operated at lower pressures, for example, at about ambient pressure. The catalyst residence time in the regenerator is about 0.1 to 1 hr and typically 0.5 to 1 hr.

Under the regeneration zone conditions of temperature and pressure the alkyl aromatic hydrocarbon product that is contained in the catalyst pores and catalyst voids is stripped from the catalyst and recovered. The coke deposits which are highly unsaturated high boiling hydrocarbons at least partially catalytically react with the hydrogen regeneration gas to form a wide boiling range of hydrocarbons which are recovered and which increase the overall hydrocarbon yield of the process.

The stripping efficiency and the reactivity of hydrogen with the coke deposited on the catalyst is effective in removing a major portion of the coke deposits. The regenerated catalyst is then introduced to the reaction zone and contacted with fresh feed.

OXYGEN REGENERATION

In order to regenerate the catalyst and to recover absorbed hydrocarbon product, a portion of the partially deactivated catalyst containing the deposited coke and absorbed hydrocarbon product contained in the catalyst pores and voids is continuously or intermittently withdrawn from the upper fluidized portion of the riser reactor, e.g. from the fluidized bed, if used, and transferred to a stripping zone in which the absorbed hydrocarbons are stripped with an inert gas. The stripped catalyst is transferred to a catalyst regeneration zone in which the deposited coke is oxidatively removed by combustion of the coke with an oxygen containing gas such as air.

About 1 to 400 %/hr, preferably 5 to 200 %/hr and more preferably 10 to 150 %/hr of the catalyst inventory in the riser reactor is withdrawn for stripping and regeneration.

The partially deactivated catalyst is transferred to the stripper vessel and is maintained in the stripper vessel as a fluidized bed at a temperature of about 10° to 200° F. less than the temperature in the riser reactor. The stripper vessel is maintained at a pressure within in about plus or minus 20 psi of the pressure in the regenerator. The catalyst is maintained as a fluidized bed by the introduction of an inert stripping gas such as nitrogen or steam at a sufficient rate to fluidize the bed.

The partially deactivated catalyst in the stripping zone is stripped of substantially all of the alkyl aromatic product, which is recovered, leaving on the catalyst substantially only the deposited coke.

The stripped catalyst is withdrawn from the stripping zone and is transferred to the catalyst regeneration zone in which the catalyst is maintained in a fluidized bed. The partially deactivated catalyst is contacted in the fluidized bed with an oxygen containing regeneration gas, such as air, to effect combustion of the coke deposited on the catalyst and removal of the coke from the catalyst and regeneration of the catalyst.

The regeneration gas comprises an oxygen containing gas. The preferred regeneration gas is air which contains about 21% oxygen, because of its ready availability and low cost. A readily available refinery source of air regeneration gas is from the air regeneration gas feed to the FCC catalyst regenerator unit.

A sufficient excess amount of the oxygen containing regenerating gas is fed to the bottom of the regenerator through a distribution plate to the regeneration zone to maintain a temperature in the regeneration zone of 700° to 1000° F. (371° to 538° C.), preferably 700° to 950° F. (371° to 510° C.), and more preferably 800° to 900° F. (427° to 482° C.) and to provide sufficient fluidizing gas to maintain the catalyst in a fluidized bed. Cooling coils may be used in the regenerator to help control the regeneration temperature. The regeneration zone can be operated at a higher or lower pressure than the riser reactor. The pressure in the regenerator is maintained at 30 to 450 psig (310 to 3200 pKa), for example, 30 to 200 psig (310 to 1480 pKa) and typically at about the pressure of riser reactor. The catalyst particles are disengaged from the fluidizing gas, including the combustion products of the coke and oxydizing gas, in the top dilute phase of the regeneration zone by one or more gas-solid separation cyclones and the separated catalyst is returned to the regeneration zone fluidized catalyst bed. The excess oxygen in the regenerating gas and the combustion products including carbon dioxide and water are removed from the regenerator as effluent gases.

The effluent gases can be conveniently fed to the FCC catalyst regenerator unit in which the excess oxygen is burned.

The medium pore molecular sieve zeolite catalyst is regenerated in the regeneration zone by the combustion and removal of substantially all of the coke deposited on the catalyst. The regenerated catalyst contains only a small residual amount of carbon in the amount of 0.001 to 0.2 wt %, preferably 0.01 to 0.1 wt % and more preferably 0.01 to 0.05 wt % based on the weight of catalyst and is withdrawn from the regeneration zone and introduced to the reaction zone and contacted with fresh aromatic and olefin feed.

An oxidative regeneration process that can be used in accordance with the present invention is described in the copending application Ser. No. 07/428,715 filed Oct. 10, 1990 which is assigned to the common assignee and which is incorporated herein by reference thereto.

Preferred embodiments of the present invention are described with reference to FIGS. 2 and 3 of the drawings.

Figure 2:
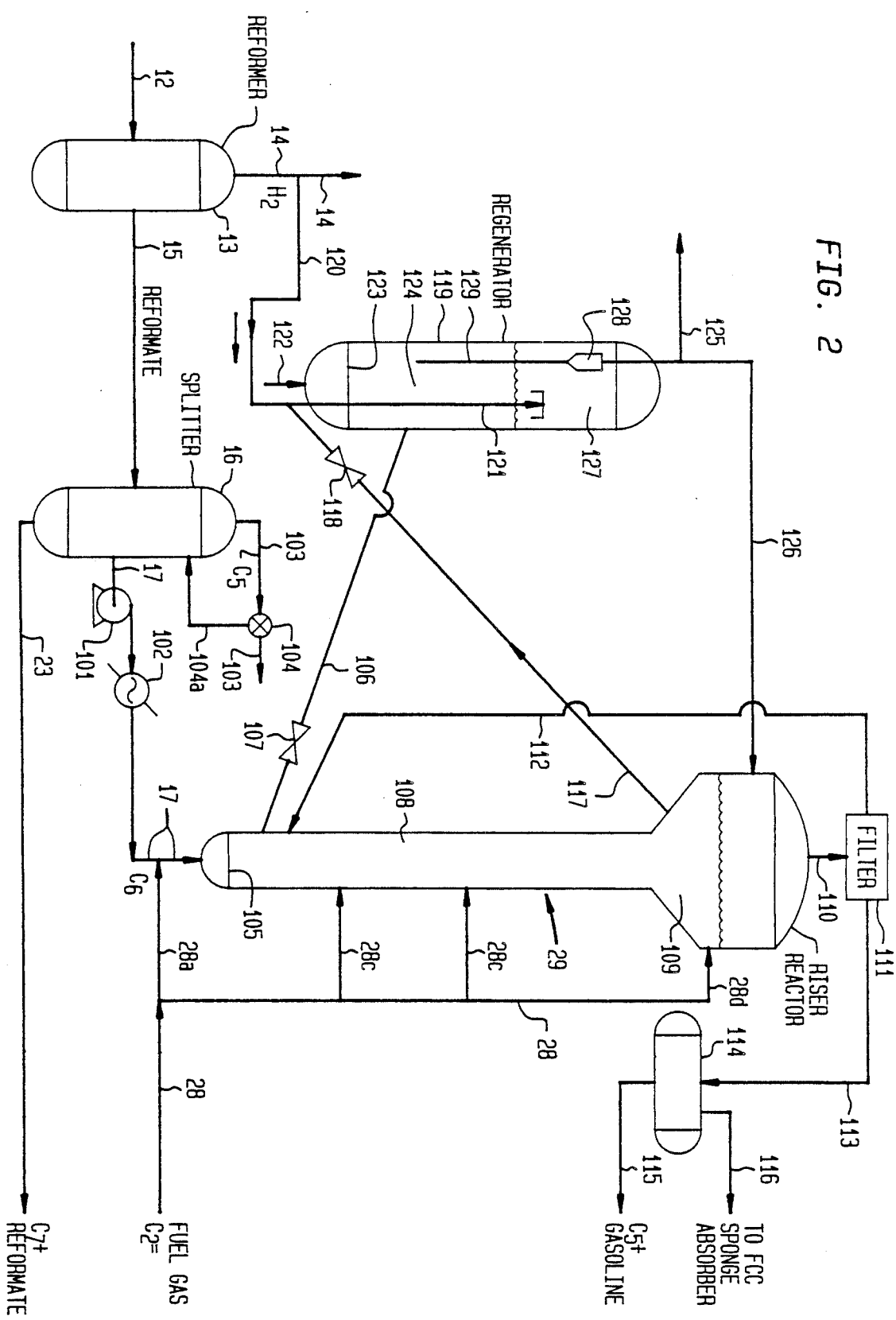
FIG. 2 of the drawings is a schematic representation of a fluidized catalyst reaction zone process and apparatus including a multiple feed injection riser reactor and a hydrogen containing gas catalyst regenerator.

Referring to FIG. 2 of the drawings a hydrotreated naphtha stream is passed through line 12 to a reforming zone 13 wherein it is catalytically reformed to produce a reformate containing $C_6$ to $C_8$ aromatic hydrocarbons and $C_6^+$ paraffinic hydrocarbons, $C_9^+$ aromatic hydrocarbons and hydrogen. The hydrogen is removed overhead in line 14. The catalytic reformate is fed through line 15 to a splitter 16 in which a portion of the $C_6^+$ paraffinic hydrocarbons can be removed through line 23 and fed to the gasoline product pool. The $C_6$ to $C_8$ aromatic hydrocarbons are removed through line 17 via pump 101 and heat exchanger 102 to distribution plate 105 in the bottom of riser reactor 29. The heat exchanger 102 preheats the $C_6$ to $C_8$ reformate prior to feeding it to the riser reactor. A $C_5$ paraffin stream can be removed through line 103 and via valve means 104 and sent to the gasoline pool. The remainder of the $C_5$ paraffins can be recycled through line 104a to the splitter 16.

A $C_4^-$ light olefin fuel gas from the FCC is fed through line 28 to the riser reactor. The fuel gas feed line 28 is separated into three portions in lines 28a, 28b and 28c. About 20 to 50% of the $C_4^-$ fuel gas is fed through line 28a and mixed with the $C_6$-$C_8$ reformate feed in line 17 and fed to the distribution plate 105 in the bottom of the riser reactor. About 20 to 40% of the $C_4^-$ fuel gas feed is fed through line 28b at an intermediate point in the height of the riser section of the reactor and the remaining about 20 to 40% of the $C_4^-$ fuel gas feed is fed at an upper point in the height of the riser section of the reactor through line 28c and through line 28d in the upper fluidized catalyst bed section. The $C_4^-$ fuel gas feed is distributed through lines 28a, 28b, 28c and 28d in a manner such that the weight ratio of $C_6$ to $C_8$ aromatics to $C_2$ and $C_3$ olefins in the fuel gas feed in the riser section and the upper fluidized catalyst bed section of the reactor during the reaction is maintained at about 12:1 to 15:1.

The $C_6$-$C_8$ aromatics and the $C_4^-$ fuel gas are contacted with regenerated ZSM-5 catalyst fed to the bottom of riser reactor 29 through catalyst return line 106 via flow control means 107 and with recycled catalyst fed through catalyst recycle line 112. The regenerated and recycled catalyst are lifted in the riser section 108 of the reactor to the upper fluidize catalyst bed section 109. The $C_6$-$C_8$ aromatics, the $C_4^-$ fuel gas and the alkyl aromatic product act as the lift gas for the catalyst in the riser section of the reactor.

The alkylation reaction is carried out primarily in the riser section 108 at a temperature of 600° to 700° F. (315° to 371° C.) and at a pressure of 150 to 250 psig (1135 to 1825 kPa).

The reaction heat can be partially or completely removed from the reaction zone by using cold or only partially preheated reformate and cold or only partially preheated $C_4^-$ fuel gas feed.

The transfer gas velocity in the riser section of the reactor is 10 to 20 ft/sec (3 to 6 m/sec). A dilute solids gas phase is withdrawn from the top of the reactor and fed to a gas solids separation zone 111 which contains a sintered metal filter and in which the solid catalyst particles are disengaged and separated from the hydrocarbon product gas. All of or at least a portion of the separated catalyst particles are returned to the bottom of the riser reactor through catalyst recycle line 112 and mixed with regenerated catalyst introduced through catalyst return line 106. The separated hydrocarbon product is withdrawn through line 113 and fed to separation vessel 114. The $C_5^+$ gasoline hydrocarbon stream containing the alkyl aromatic product is withdrawn through line 115. An overhead stream containing $C_4^-$ hydrocarbons is withdrawn through line 116 and is fed to the FCC sponge absorber.

The residence time of the reformate feed and $C_4^-$ fuel gas feed in the riser reactor is about 3 to 7 sec.

The catalyst alkylation conversion reaction converts a minor portion of the light olefin feed to coke by-products which deposit on the catalyst and partially deactivate the catalyst. Also during the reaction alkyl aromatic product is absorbed in the catalyst pores and voids.

In order to regenerate the catalyst and to recover the absorbed hydrocarbon product, a portion of the partially deactivated catalyst is continuously withdrawn from the upper fluidized bed section of the reactor and transferred by catalyst outlet means 117 through valve control means 118 to catalyst regenerator 119.

About 12 to 170%/hr of the catalyst inventory in the reactor is withdrawn for regeneration. The partially deactivated catalyst as mentioned above contains deposited coke and absorbed hydrocarbon product.

The partially deactivated catalyst in line 117 is entrained in hydrogen regeneration gas provided from the reformer 13 via line 120 and transported via riser 121 to the top portion of the regenerator vessel 119. The main portion of the hydrogen regeneration gas is introduced into the regenerator 119 via line 122 and distributor plate 123 to effect fluidization of the catalyst in the fluidized bed 124. A sufficient amount of hydrogen regeneration gas is fed to the regenerator to maintain the catalyst as a fluidized bed.

The temperature in the regenerator is maintained at about 700° to 1200° F. (371° to 649° C.) and at about the same pressure as the riser reactor.

The hydrogen regeneration gas strips the absorbed hydrocarbon product contained in the catalyst pores and the catalyst voids, including alkyl aromatic hydrocarbons from the catalyst. The hydrogen at the same time at least partially reacts with the deposited coke to hydrogenate the coke to form hydrocarbons and to remove a major portion of the coke from the catalyst. The stripped hydrocarbons and the hydrogenated coke hydrocarbons are removed from the regenerator 119 through line 125 and taken for separation and further processing. Alternatively all or a portion of the withdrawn hydrocarbons can be returned to the riser reactor through line 126. Catalyst particles in the dilute phase 127 of the regenerator are disengaged from the fluidizing gas in cyclone separator 28 and returned to the regeneration zone through dip leg 129.

The effluent gases from the regenerator can be treated to separate the hydrogen regeneration gas from the hydrocarbon products and the separated hydrogen can be recycled to the regenerator or recovered.

The regenerated catalyst containing only a small residual amount of carbon is withdrawn from the regenerator through catalyst withdrawal line 106 via valve control means 107 and fed to the bottom of the riser reactor 29 and is contacted with fresh reformate and $C_4^-$ fuel gas feed.

Figure 3:
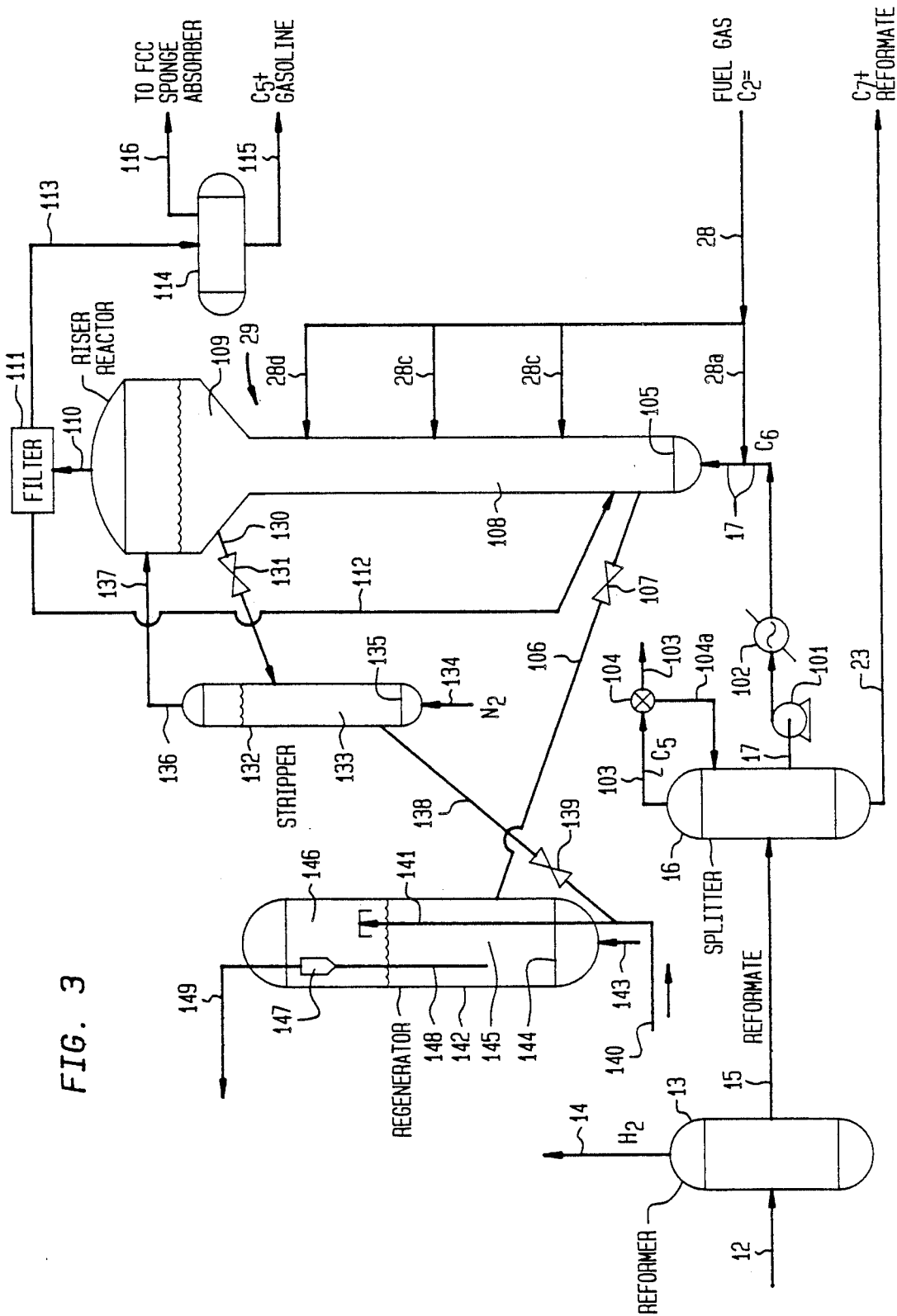
FIG. 3 of the drawings is a schematic representation of a fluidized catalyst reaction zone process and apparatus including a multiple feed injection riser reactor, a catalyst stripper and an oxygen containing gas catalyst regenerator.

Referring to FIG. 3 of the drawings a hydrotreated naphtha stream is passed through line 12 to a reforming zone 13 wherein it is catalytically reformed to produce a reformate containing $C_6$ to $C_8$ aromatic hydrocarbons and $C_6^+$ paraffinic hydrocarbons, $C_9^+$ aromatic hydrocarbons and hydrogen. The hydrogen is removed overhead in line 14. The catalytic reformate is fed through line 15 to a splitter 16 in which a portion of the $C_6^+$ paraffinic hydrocarbons can be removed through line 23 and fed to the gasoline product pool. The $C_6$ to $C_8$ aromatic hydrocarbons are removed through line 17 via pump 101 and heat exchange 102 to distribution plate 105 in the bottom of riser reactor 29. The heat exchanger 102 preheats the $C_6$ to $C_8$ reformate prior to feeding it to the riser reactor. A $C_5$ paraffin stream can be removed overhead through line 103 and via valve means 104 and sent to the gasoline pool. The remainder of the $C_5$ paraffins can be recycled via line 104a to the splitter 16.

A $C_4^-$ light olefin fuel gas from the FCC is fed through line 28 to the riser reactor. The fuel gas feed line 28 is separated into four portions in lines 28a, 28b, 28c and 28d. About 20 to 60% of the $C_4^-$ fuel gas is fed through line 28a and mixed with the $C_6$-$C_8$ reformate feed in line 17 and fed to the distribution plate 105 in the bottom of the riser reactor. About 20 to 40% of the $C_4^-$ fuel gas feed is fed through line 28b at an intermediate point in the height of the riser section of the reactor. About 20 to 40% of the $C_4^-$ fuel gas feed is fed at about mid-point in the riser section of the reactor through line 28c. The remaining about 20 to 40% of the $C_4^-$ fuel gas feed is fed at an upper point in the height of the riser section of the reactor through line 28d. The $C_4^-$ fuel gas feed is distributed through lines 28a, 28b, 28c and 28d in a manner such that the weight ratio of $C_6$ to $C_8$ aromatics to $C_2$ and $C_3$ olefins in the fuel gas feed in the riser section of the reactor is maintained at 12:1 to 15:1 during the reaction.

The $C_6$-$C_8$ aromatics and the $C_4^-$ fuel gas are contacted with regenerated ZSM-5 catalyst fed to the bottom of riser reactor 29 through catalyst return line 106 via flow control means 107 and with recycled catalyst fed through catalyst recycle line 112. The regenerated catalyst is lifted in the riser section 108 of the reactor to the upper fluidized catalyst bed section 109. The $C_6$-$C_8$ aromatics, the $C_4^-$ fuel gas and the alkyl aromatic product act as the lift gas for the catalyst in the riser section of the reactor.

The alkylation reaction is carried out primarily in the riser section 108 at a temperature of about 600° to 700° F. (315° to 371° C.) and at a pressure of abut 150 to 250 psig (1135 to 1825 kPa).

The reaction heat can be partially or completely removed from the reaction zone by using cold or only partially preheated reformate and cold or only partially preheated $C_4^-$ fuel gas feed.

The transfer gas velocity in the riser section of the reactor is 10 to 20 ft/sec (3 to 6 m/sec). A dilute solids gas phase is withdrawn from the top of the reactor and fed to a gas solids separation zone 111 which contains a sintered metal filter and in which the solid catalyst particles are disengaged and separated from the hydrocarbon product gas. All or at least a portion of the separated catalyst particles are returned to the bottom of the riser reactor through catalyst recycle line 112 and mixed with regenerated catalyst introduced through catalyst return line 106. The separated hydrocarbon product is withdrawn through line 113 and fed to separation vessel 114. The $C_5^-$ hydrocarbon stream containing the alkyl aromatic product is withdrawn through line 115. An overhead stream containing $C_4^-$ hydrocarbons is withdrawn through line 116 and is recycled to the FCC sponge absorber.

The residence time of the reformate feed and $C_4^-$ fuel gas feed in the riser reactor is about 3 to 7 sec.

The catalytic alkylation conversion reaction converts a minor portion of the light olefin feed to coke by-products which deposit on the catalyst and partially deactivate the catalyst. Also during the reaction alkyl aromatic product is absorbed in the catalyst pores and voids.

In order to regenerate the catalyst and to recover the absorbed hydrocarbon product, a portion of the partially deactivated catalyst is continuously withdrawn from the upper fluidized bed section of the reactor and transferred by catalyst outlet means 130 through valve control means 131 to catalyst stripper vessel 132. About 5 to 150 %/hr of the catalyst inventory in the reactor is withdrawn for stripping and regeneration. The partially deactivated catalyst contains deposited coke and absorbed hydrocarbon product.

The partially deactivated catalyst is maintained as a fluid bed in the stripper zone 133 at a pressure within about plus or minus 20 psi of the pressure in the regenerator and is contacted with an inert stripping gas such as nitrogen. The nitrogen stripping gas is introduced into the bottom of the stripping zone through line 134 and distribution plate 135 at a sufficient rate to maintain the fluidized bed in stripping zone 133 and to maintain a stripping gas velocity through the fluidized bed. The partially deactivated catalyst in the stripping zone is stripped of substantially all of the hydrocarbon product, leaving on the catalyst substantially only deposited coke. The stripped hydrocarbon product is returned to the reactor through outlet line 136 and 137 for recovery of the hydrocarbon.

The stripped catalyst containing deposited coke is withdrawn from the stripping zone through stripped catalyst outlet line 138 and valve control means 139. The stripped catalyst is entrained in an air regeneration gas provided via line 140 and transported via riser 141 to the top portion of the regenerator vessel 142. The main portion of the regeneration gas is introduced into the regenerator 142 via line 143 and distributor plate 144 to effect fluidization of the stripped catalyst in the fluidized bed 145 of the regeneration zone.

The stripped partially deactivated catalyst is contacted in the fluidized bed of the regenerator 142 with an oxygen containing regeneration gas such as air to effect combustion of the coke and removal of the coke from the catalyst and regeneration of the catalyst. A sufficient amount of the oxygen containing regenerating gas is fed to the regeneration zone via line 143 and distribution plate 144 to maintain the catalyst as a fluidized bed. The temperature in the fluidized bed is maintained at about 800° to 900° F. (427 to 482° C.) by controlling the amount of oxygen containing gas introduced to the regeneration zone. The pressure in the regenerator is about the same pressure as that in the riser reactor. The regeneration gas advantageously can be provided from the air regeneration gas feed to the FCC catalyst regenerator.

The catalyst particles are disengaged from the fluidizing gas, including combustion products of the coke and oxydizing gas, in the top dilute phase 146 of the regenerator in cyclone separator 147. The separated catalyst is returned to the regeneration zone through dip leg 148. The effluent gases containing the regeneration combustion gases and excess oxygen is withdrawn from the regenerator through effluent gas outlet line 149.

The effluent gases from the catalyst regenerator in line 149 can conveniently be fed to a FCC catalyst regenerator in which the excess oxygen is burned.

The catalyst is regenerated in the regeneration zone 145 by the combustion and removal of substantially all of the coke deposited on the catalyst. The residence time of the catalyst in the regeneration zone is 20 to 180 minutes. The regenerated catalyst containing only a small residual amount of carbon typically less than 0.05 wt %, for example, in the amount of about 0.01 to 0.05 wt % based on the weight of catalyst is withdrawn from the regenerator through catalyst withdrawal line 106 via valve control means 107 and fed to the bottom of the riser reactor 29 and is contacted with fresh reformate and $C_4^-$ fuel gas feed.

The temperature can be controlled in the riser reactor by aromatic feed and/or olefin feed preheat. Part or all of the reaction heat can be removed from the riser reactor by using cool feed, whereby reactor temperature can be controlled by adjusting feed temperature. The temperature in the stripping vessel can be controlled by controlling the temperature of the nitrogen stripping gas.

The stripped hydrocarbons in line 136 can be treated to separate and recycle the nitrogen to the stripping zone prior to feeding the stripped hydrocarbons to riser reactor 29. Alternatively the stripped hydrocarbons can be separately treated to recover the nitrogen and hydrocarbons.

The present invention is further illustrated by the following example.

EXAMPLE

The process is carried out in a fluidized bed riser reactor using the apparatus and method of the FIG. 2 embodiment of the invention. An HZSM-5 zeolite catalyst having an average steady state alpha value of 5-10 is used. The temperature in the riser section of the reactor is about 850° F. (454° C.) and the pressure is about 150 psig (1135 kPa). The olefin feed is fed through three injection feed points spaced along the height of the riser reactor. The olefin feed is distributed through the three injection points in a manner such as to maintain an aromatic to olefin weight ratio in the riser section of the reactor of 7:1. The reformate feed is fed to the bottom of the riser section of the reactor at a sufficient rate to maintain the desired aromatic to olefin weight ratio in the riser reactor.

The reaction is carried out while maintaining the catalyst in the riser section of the reactor in the transport regime and maintaining the upper fluidize bed of the riser reactor in the turbulent bed regime.

The olefin and reformate feed stream compositions are given in Table 1 below.

TABLE 1

| Feedstream Compositions | |
|---|---|
| | Wt % |
| Olefin Gas | |
| Hydrogen | 2.3 |

TABLE 1-continued

| Feedstream Compositions | |
|---|---|
|  | Wt % |
| Ethene | 12.2 |
| Propene | 12.1 |
| Reformate |  |
| Benzene | 5 |
| Toluene | 11.5 |
| C$_8$ Aromatics | 18 |

For purposes of comparison the process is repeated with the exception that all of the olefin feed is introduced in the bottom of the riser reactor and mixed with the reformate feed. The weight ratio of aromatics to olefins in the riser section of the reactor as a result of the single point injection of the olefin feed is about 3.5 to 1.

The effluent hydrocarbon gas stream in each case is analyzed and the results obtained are reported in Table 2 below.

TABLE 2

|  | Wt Ratio Aromatics/ Olefins | Wt % Conversion Aromatic Feed To Alkyl Aromatics | Wt % Conversion Olefin Feed To Alkyl Aromatics | Wt % Coke Make Based On Olefin Feed |
|---|---|---|---|---|
| Invention | 7:1 | 30 | 90 | 0.007 |
| Comparison | 3.5:1 | 26 | 85 | 0.030 |

The above data show that by carrying out the process of the present invention of maintaining a high weight ratio of aromatic to olefin feed using multi olefin feed injection in a riser reactor that there is an increase in the conversion of aromatic hydrocarbons and an increase in the conversion of olefin hydrocarbons to alkyl aromatic hydrocarbons and a substantial decrease in the coke make. The data show that undesirable coke make is reduced by more than 75%.

Having thus generally described the present invention and discussed the preferred embodiments in support thereof, it is to be understood that no undue restrictions are to be imposed by reason thereof except as defined by the following claims.

What is claimed is:

1. A process for the production of gasoline which comprises contacting a feed stream comprising C$_4^-$ olefin hydrocarbons with a feed stream comprising C$_6$ to C$_8$ aromatic hydrocarbons at an aromatic to olefin weight ratio of 5:1 to 20:1 over a fluidized zeolite catalyst at a temperature of 350° to 900° F. and a pressure of 20 to 650 psig in a riser reactor having multiple olefin feed injection points to alkylate the C$_6$-C$_8$ aromatics with the olefins to form C$_7$ to C$_{11}$ alkyl aromatic hydrocarbon gasoline products, wherein the multiple olefin feed injection points are spaced along the height of the riser reactor and the aforesaid aromatic to olefin weight ratio is maintained throughout the riser reactor and withdrawing a portion of the catalyst from the riser for regeneration of the catalyst, said withdrawn catalyst containing only a minor amount of deposited coke.

2. The process of claim 1 wherein the riser reactor comprises a lower riser section and an upper fluid bed section and the multiple olefin feed injection points are spaced along the height of the riser section or along the height of the riser section and the upper fluidized catalyst bed section of the reactor.

3. The process of claim 1 wherein the olefin feed comprises 1 to 90 wt. % ethene.

4. The process of claim 1 wherein the zeolite catalyst comprises HZSM-5 zeolite catalyst.

5. The process of claim 1 wherein coke by-products are deposited on the catalyst and the coke make is less than about 0.3 wt % of the olefin feed.

6. The process of claim 1 wherein the C$_4^-$ hydrocarbon feed stream comprises 8 to 50 wt. % ethene and 3 to 50 wt. % propene and the aromatics feed stream comprises 10 to 95 wt. % C$_6$ to C$_8$ aromatics.

7. The process of claim 1 wherein the catalytic alkylation reaction converts a minor portion of the light olefin feed to coke by-products which deposit on the catalyst and partially deactivate the catalyst and during which hydrocarbon product is absorbed by the catalyst, which further comprises regeneration of the catalyst by withdrawing a portion of the catalyst from the riser reactor and contacting the withdrawn catalyst in a fluidized bed catalyst regeneration zone with a hydrogen containing regeneration catalyst at a temperature of about 700° to 1200° F. to strip the absorbed hydrocarbon products from the catalyst and to hydrogenate the coke deposits and convert the coke deposits to hydrocarbons and remove a major portion of the coke deposits from the catalyst to regenerate the catalyst and returning the regenerated catalyst to the riser reactor.

8. The process of claim 1 wherein the catalytic alkylation reaction converts a minor portion of the light olefin feed to coke by-products which deposit on the catalyst and partially deactivate the catalyst and during which hydrocarbon product is absorbed by the catalyst, which further comprises regeneration of the catalyst by withdrawing a portion of the catalyst from the riser reactor and contacting the withdrawn catalyst in a catalyst stripping zone with an inert stripping gas to strip from the catalyst the absorbed hydrocarbon product, removing the stripped catalyst from the stripping zone and transferring the catalyst containing coke deposits to a fluidized bed catalyst regeneration zone in which the catalyst is contacted with an oxygen containing regeneration gas at a temperature of about 700° to 950° F. to effect combustion of the coke and removal of coke from the catalyst and regeneration of the catalyst and returning the regenerated catalyst to the riser reactor.

9. A process for the production of gasoline which comprises contacting a fuel gas from a fluid catalytic cracking process, comprising C$_4^-$ hydrocarbons including ethene and propene, with a catalytic reformate feed stream, comprising C$_6$ to C$_8$ aromatic hydrocarbons, at an aromatic to olefin weight ratio of 7:1 to 20:1 over a zeolite catalyst at a temperature of 500° to 750° F. and pressure of 120 to 420 psig in a riser reactor having multiple olefin feed injection points to alkylate the C$_6$-C$_8$ aromatics with the said olefins to form C$_7$ to C$_{11}$ aromatic hydrocarbon gasoline products, wherein the multiple olefin feed injection points are spaced along the height of the riser reactor and the aforesaid aromatic to olefin weight ratio is maintained throughout the riser reactor and withdrawing a portion of the catalyst from the riser reactor for regeneration of the catalyst, said withdrawn catalyst containing only a minor amount of deposited coke.

10. The process of claim 9 wherein the riser reactor comprises a lower riser section and an upper fluid bed section and the multiple feed injection points are spaced along the height of the riser section or along the height of the riser section and the upper fluidized catalyst bed section of the reactor.

11. The process of claim 9 wherein the zeolite catalyst comprises HZSM-5 zeolite catalyst.

12. The process of claim 9 wherein the weight ratio of aromatic hydrocarbons to olefins is at least 10:1.

13. The process of claim 9 wherein the $C_4^{31}$ hydrocarbon feed stream comprises 8 to 35 wt. % ethene and 3 to 40 wt. % propene and the aromatic hydrocarbon feed stream comprises 35 to 75 wt. % $C_6$ to $C_8$ aromatics.

14. A process for the production of gasoline which comprises
feeding a first hydrocarbon naphtha distillate stream to a hydrotreating zone operated under hydrotreating conditions and recovering a hydrotreated effluent stream;
feeding the hydrotreated effluent stream to a catalytic reforming zone operated under reforming conditions to recover a reforming zone reformate stream comprising $C_6$ to $C_8$ aromatic hydrocarbons, $C_5$ to $C_8$ paraffinic hydrocarbons and hydrogen;
feeding a second hydrocarbon vacuum gas oil stream into a fluidized catalytic cracking zone to recover an overhead fuel gas vapor stream comprising $C_4^{31}$ hydrocarbons including ethene and propene;
contacting at least a portion of the catalytic reformate stream comprising in $C_6$ to $C_8$ aromatics and the $C_4^{31}$ fuel gas stream comprising ethene and propene at an aromatic to olefin weight ratio of 10:1 to 15:1 over a zeolite catalyst in a riser reactor having multiple olefin feed injection points to alkylate the $C_6$-$C_8$ aromatics with the olefins to form $C_7$ to $C_{11}$ alkyl aromatic hydrocarbon gasoline products, wherein the aforesaid aromatic to olefin weight ratio is maintained throughout the riser reactor and withdrawing a portion of the catalyst from the riser reactor for regeneration of the catalyst, said withdrawn catalyst containing only a minor amount of deposited coke.

15. The process of claim 14 wherein the riser reactor comprises a lower riser section and an upper fluid bed section and the multiple olefin feed injection points are spaced along the height of the riser section or along the height of the riser section and the upper fluidized catalyst bed section of the reactor.

16. The process of claim 14 wherein the catalyst in the fluidized catalytic cracking zone is withdrawn and transferred to a catalyst regeneration zone in which it is contacted with an oxygen containing regeneration gas that is fed to the regeneration zone to regenerate the fluidized catalytic cracking zone catalyst.

17. The process of claim 14 wherein the catalytic reformate stream comprising $C_6$ to $C_8$ aromatics and the $C_4^-$ fuel gas stream comprising ethene and propene are contacted over the zeolite catalyst at a temperature of about 600° to 750° F. and a pressure of about 150 to 250 psig.

18. The process of claim 14 wherein the olefin feed comprises 8 to 35 wt. % ethene.

19. The process of claim 14 wherein the zeolite catalyst comprises HZSM-5 zeolite catalyst.

20. The process of claim 14 wherein the olefin feed is fed to the process through 2 to 4 olefin feed injection points.

21. The process of claim 14 wherein the $C_4^-$ hydrocarbon feed stream comprises 8 to 35 wt % ethene and 3 to 40 wt % propene and the catalytic reformate stream comprises 35 to 75 wt % $C_6$ to $C_8$ aromatics.

22. The process of claim 14 wherein the aromatic hydrocarbon feed stream comprises 2 to 60 wt % benzene, 1 to 40 wt% toluene.

23. The process of claim 14 wherein the catalytic alkylation reaction converts a minor portion of the light olefin feed to coke by-products which deposit on the catalyst and partially deactivate the catalyst and during which hydrocarbon product is absorbed on the catalyst which further comprises regeneration of the catalyst by withdrawing a portion of the catalyst from the riser reactor and contacting the withdrawn catalyst in a fluidized bed catalyst regeneration zone with a hydrogen containing regeneration gas at a temperature of 700° to 1000° F. to strip the absorbed hydrocarbon products from the catalyst and to hydrogenate the coke deposits and convert the coke deposits to hydrocarbons and remove a major portion of the coke deposits from the catalyst to regenerate the catalyst and returning the regenerated catalyst to the riser reactor.

24. The process of claim 23 wherein the hydrogen gas by-product from a catalytic reforming zone is used as the hydrogen containing regeneration gas.

25. The process of claim 14 wherein the catalytic alkylation reaction converts a minor portion of the light olefin feed to coke by-products which deposit on the catalyst and partially deactivate the catalyst and during which hydrocarbon product is absorbed by the catalyst which further comprises regeneration of the catalyst by withdrawing a portion of the catalyst from the riser reactor and contacting the withdrawn catalyst in a catalyst stripping zone with an inert stripping gas to strip from the catalyst the absorbed hydrocarbon product, removing the stripped catalyst from the stripping zone and transferring the catalyst containing coke deposits to a fluidized bed catalyst regeneration zone in which the catalyst is contacted with an oxygen containing regeneration gas at a temperature of about 800° to 900° F. to effect combustion of coke and removal of the coke from the catalyst and regeneration of the catalyst and returning the regenerated catalyst to the riser reactor.

26. The process of claim 25 wherein oxygen containing regeneration gas feed to a fluidized catalytic cracking zone catalyst regeneration zone is used as the regeneration gas.

27. A process for the production of gasoline which comprises contacting a feed stream comprising $C_4^-$ olefin hydrocarbons with a feed stream comprising $C_6$ to $C_8$ aromatic hydrocarbons at an aromatic to olefin weight ratio of 7:1 to 20:1 over a fluidized zeolite catalyst at a temperature of 350° to 900° F. and a pressure of 20 to 650 psig in a riser reactor having multiple olefin feed injection points to alkylate the $C_6$-$C_8$ aromatics with the olefins to form $C_7$ to $C_{11}$ alkyl aromatic hydrocarbon gasoline products, said multiple feed injection points are spaced along the height of the riser reactor whereby the aforesaid aromatic to olefin weight ratio is maintained throughout the riser reactor, wherein the catalytic alkylation reaction converts a minor portion of the light olefin feed to coke by-products which deposit on the catalyst and partially deactivate the catalyst and during which hydrocarbon product is absorbed by the catalyst, which further comprises regeneration of the catalyst by withdrawing a portion of the catalyst from the riser reactor and contacting the withdrawn catalyst in a fluidized bed catalyst regeneration zone with a hydrogen containing regeneration catalyst at a temperature of about 700° to 1200° F. to strip the absorbed hydrocarbon products from the catalyst and to hydrogenate the coke deposits and convert the coke deposits to hydrocarbons and remove a major portion of the coke deposits from the catalyst to regenerate the catalyst and returning the regenerated catalyst to the riser reactor.

28. A process for the production of gasoline which comprises contacting a feed stream comprising $C_4^-$ olefin hydrocarbons with a feed stream comprising $C_6$ to $C_8$ aromatic hydrocarbons at an aromatic to olefin weight ratio of 7:1 to 20:1 over a fluidized zeolite catalyst at a temperature of 350° to 900° F. and a pressure of 20 to 650 psig in a riser reactor having multiple olefin feed injection points to alkylate the $C_6$–$C_8$ aromatics with the olefins to form $C_7$ to $C_{11}$ alkyl aromatic hydrocarbon gasoline products, said multiple feed injection points are spaced along the height of the riser reactor whereby the aforesaid aromatic to olefin weight ratio is maintained throughout the riser reactor, wherein the catalytic alkylation reaction converts a minor portion of the light olefin feed to coke by-products which deposit on the catalyst and partially deactivate the catalyst and during which hydrocarbon product is absorbed by the catalyst, which further comprises regeneration of the catalyst by withdrawing a portion of the catalyst from the riser reactor and contacting the withdrawn catalyst in a catalyst stripping zone with an inert stripping gas to strip from the catalyst the absorbed hydrocarbon product, removing the stripped catalyst from the stripping zone and transferring the catalyst containing coke deposits to a fluidized bed catalyst regeneration zone in which the catalyst is contacted with an oxygen containing regeneration gas at a temperature of about 700° to 950° F. to effect combustion of the coke and removal of coke from the catalyst and regeneration of the catalyst and returning the regenerated catalyst to the riser reactor.

* * * * *

UNITED STATES PATENT AND TRADEMARK OFFICE
CERTIFICATE OF CORRECTION

PATENT NO. : 4,992,607

DATED : February 12, 1991

INVENTOR(S) : Harandi et al

It is certified that error appears in the above-identified patent and that said Letters Patent is hereby corrected as shown below:

Column 19, claim 1, line 60, insert "reactor" after --riser--.

Column 21, claim 13, line 7, "$C_4 31$" should be --$C_4^-$--.

Column 21, claim 14, line 25, "$C_4 31$" should be --$C_4^-$--.

Column 21, claim 14, lind 29, "$C_4 31$" should be --$C_4^-$--.

Signed and Sealed this

Fourteenth Day of July, 1992

*Attest:*

DOUGLAS B. COMER

*Attesting Officer*   *Acting Commissioner of Patents and Trademarks*